(12) United States Patent
Greene et al.

(10) Patent No.: US 9,165,113 B2
(45) Date of Patent: Oct. 20, 2015

(54) SYSTEM AND METHOD FOR QUANTITATIVE ASSESSMENT OF FRAILTY

(75) Inventors: Barry R. Greene, Dublin (IE); Alan D. O'Donovan, Meath (IE)

(73) Assignee: INTEL-GE CARE INNOVATIONS LLC, Roseville, CA (US)

( * ) Notice: Subject to any disclaimer, the term of this patent is extended or adjusted under 35 U.S.C. 154(b) by 786 days.

(21) Appl. No.: 13/283,337

(22) Filed: Oct. 27, 2011

(65) Prior Publication Data

US 2013/0110475 A1 May 2, 2013

(51) Int. Cl.
*A61B 5/11* (2006.01)
*G06F 19/00* (2011.01)

(52) U.S. Cl.
CPC .......... *G06F 19/3431* (2013.01); *A61B 5/1117* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 6,820,025 B2 * | 11/2004 | Bachmann et al. | 702/94 |
| 8,961,439 B2 * | 2/2015 | Yang et al. | 600/595 |
| 2008/0146968 A1 * | 6/2008 | Hanawaka et al. | 600/595 |
| 2009/0076765 A1 * | 3/2009 | Kulach et al. | 702/141 |
| 2009/0185772 A1 * | 7/2009 | Xia et al. | 385/13 |
| 2009/0247910 A1 * | 10/2009 | Klapper | 600/595 |
| 2011/0022349 A1 * | 1/2011 | Stirling et al. | 702/141 |
| 2011/0162433 A1 * | 7/2011 | Peng et al. | 73/1.13 |
| 2011/0213278 A1 * | 9/2011 | Horak et al. | 600/595 |
| 2011/0288811 A1 * | 11/2011 | Greene | 702/141 |
| 2012/0065915 A1 * | 3/2012 | Hara et al. | 702/96 |
| 2012/0072168 A1 * | 3/2012 | Yin et al. | 702/150 |
| 2012/0253234 A1 * | 10/2012 | Yang et al. | 600/595 |
| 2012/0289791 A1 * | 11/2012 | Jain et al. | 600/301 |
| 2012/0316843 A1 * | 12/2012 | Beno et al. | 703/2 |
| 2013/0060512 A1 * | 3/2013 | Greene | 702/141 |
| 2013/0123666 A1 * | 5/2013 | Giuffrida et al. | 600/595 |
| 2013/0123669 A1 * | 5/2013 | Kinoshita et al. | 600/595 |

OTHER PUBLICATIONS

M. R. Narayanan, S. J. Redmond, M. E. Sealzi, S. R. Lord, B. G. Celler, N. H. Lovell, "Longitudinal Falls Risk Estimation using Triaxial Accelerometry" pp. 1-8, 2009.*
A. Salarian, F. B. Horak, C. Zampieri, P. C. Kuhta, J. G. Nutt, and K. Aminian, "iTUG, a Sensitive and Reliable Measure of Mobility", pp. 303-310, Jun. 2010.*

(Continued)

*Primary Examiner* — Kibrom K Gebresilassie
(74) *Attorney, Agent, or Firm* — Pillsbury Winthrop Shaw Pittman LLP

(57) ABSTRACT

Methods, systems, and apparatus for quantifying an individual's frailty level based on inertial sensor data collected from the individual. The quantified frailty level may correspond to and approximate clinical metrics of frailty, such as the Fried frailty index. A linear regression model may be used to output the quantitative frailty value based on input parameters from the inertial sensor data. The linear regression model may be initially generated from the clinically-measured frailty index values of individuals and inertial sensor data collected from them. The inertial sensor data may be collected during, for example, a timed up and go (TUG) test. Two logistic regression models may be used to output a frailty class based on input parameters from the inertial sensor data. A first logistic regression model may distinguish between robust and frail individuals. A second logistic regression model may distinguish between robust and pre-frail individuals.

8 Claims, 5 Drawing Sheets

(56) References Cited

OTHER PUBLICATIONS

D. McGrath, B. R. Greene, C. Walsh, B. Caulfield, "Estimation of minimum ground clearance (MGC) using body-worn inertial sensors", pp. 1083-1088, 2011.*

B. Greene, D. McGrath, R. O'Neill, K. J. O'Donovan, A. Burns, B. Caulfield, An Adaptive gyroscope-based algorithm for temporal gait analysis pp. 1251-1260, May 2010.*

K. O'Donovan, B. R. Greene, D. McGrath, R. O'Neill, A. Burns, B. Caulfield, Shimmer: a new tool for temporal Gait analysis, Sep. 2009, pp. 3826-3829.*

B. R. Greene, A. O'Donovan, R. R. Ortuno, L. Cogan, C. N. Scanaill, and R. A. Kenny, "Quantitative Falls Risk Assessment Using the Timed Up and Go Test", pp. 2918-2926, Dec. 2010.*

E. P. Doheny, T. G. Foran, and B. R. Greene, "A single gyroscope method for spatial gait analysis" Sep. 4, 2010, pp. 1300-1303.*

Y. Higashi, K. Yamakoshi, T. Fujimoto, M. Sekine, and T. Tamura, "Quantitative Evaluation of Movement Using the Timed Up-and-Go test". pp. 38-46, 2008.*

Y. Higashi, K. Yamakoshi, T. Fujimoto, M. Sekine, and T. Tamura, "Quantitative Evaluation of Movement using the timed Up-and-Go Test" pp. 38-46, 2008 IEEE.*

M. A. Makary, D. L. Segev, P. J. Pronovost, D. Syin, K. Bandeen-Roche, P. Patel, R. Takenaga, L. Devgan, C. G. Holzmueller, J. Tian, L. P. Fried, "Frailty as a Predictor of Surgical Outcomes in Older Patients" pp. 901-908, 2010.*

B. R. Greene, D. McGrath, K. J. O'Donovan, R. O'Neill, A. Burns, B. Caulfield, "Adaptive estimation of temporal gait parameters using body-worn gyroscopes" pp. 1296-1299, 2010.*

Fried, et al. "Frailty in Older Adults: Evidence for a Phenotype" Journal of Gerantology: Medical Sciences, 2001, vol. 56A, No. 3, pp. M146-M156.

* cited by examiner

Fig. 1A
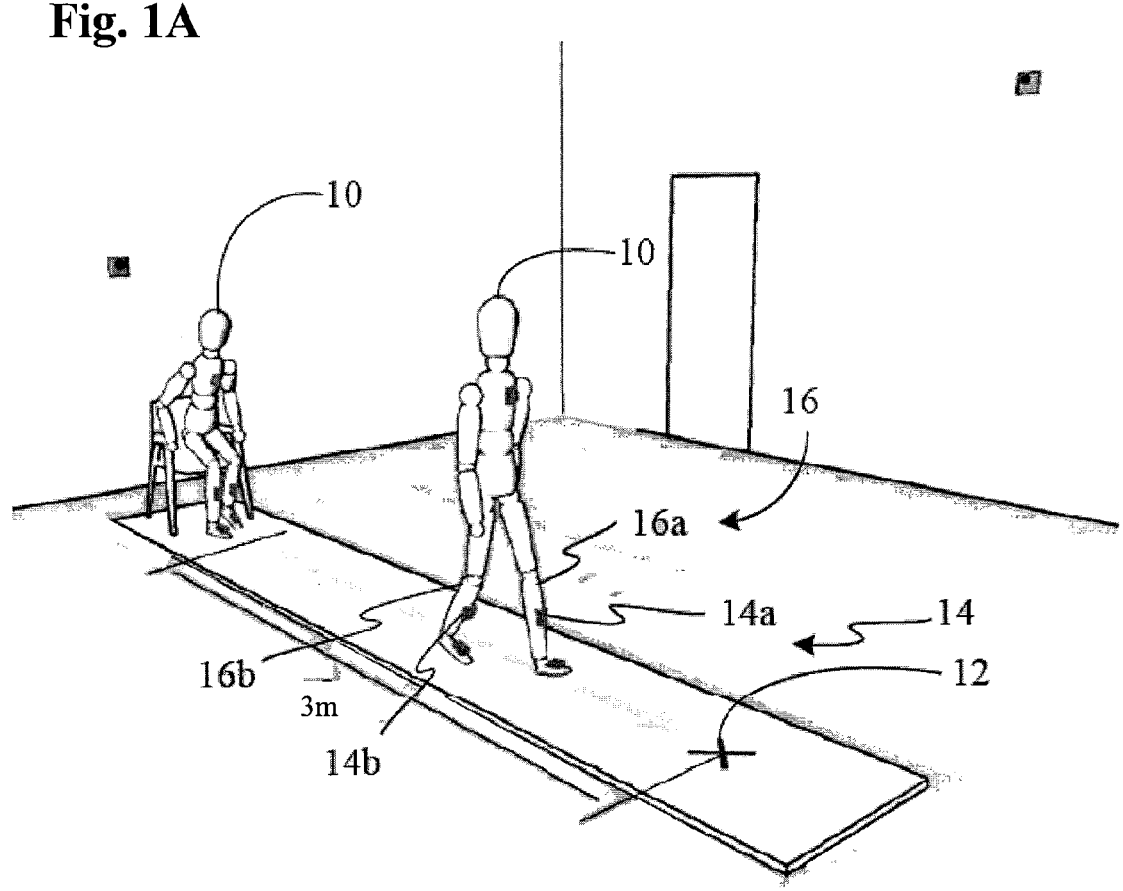
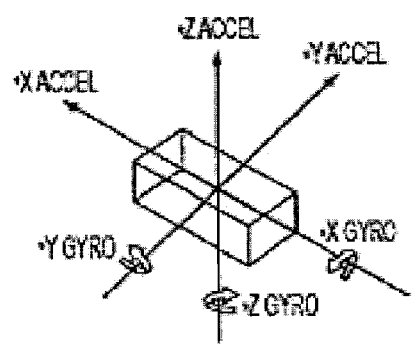
FIG. 1B

SYSTEM AND METHOD FOR QUANTITATIVE ASSESSMENT OF FRAILTY

TECHNICAL FIELD

Embodiments generally relate to frailty assessment, and more particularly to quantifying frailty based on data collected by body-worn sensors.

BACKGROUND

The concept of frailty in elderly adults has been gaining acceptance as an emerging geriatric syndrome. Although frailty is a recognizable and common phenomenon in aging, it can be a concept that is difficult to accurately define and diagnose. Frailty is a multi-factorial condition, influenced by the combination of a person's physical, psychological, and social health. Frailty has been shown to have a predictive association with important health outcomes such as first fall, first hospitalization, worsening ADL disability, worsening mobility disability, and death.

Accurate assessment of a patient's frailty level could allow for effective multi-factorial intervention. Frailty has previously been assessed using subjective clinical judgment. More recently, validated clinical scales, such as the Fried frailty index, has been used to quantify frailty levels. The Fried frailty index ranges from 0 to 5. A value of 0 is assigned to individuals considered robust. A value of 1-2 is assigned to individuals considered pre-frail, and a value of 3-5 is assigned to individuals considered frail. Assessing an individual's Fried frailty index requires, however, statistical expertise and a reference sample. The assessment further requires recognition of unintentional weight loss, weakness (e.g., low grip strength), slow walking speed, low physical activity, and/or self-monitoring for exhaustion. Such expertise and resources are often not available in a primary care setting, where primary care practitioners are often non-experts and are not trained to measure or assess clinical metrics such as the Fried frailty index.

SUMMARY OF THE INVENTION

One aspect of the invention relates to estimating an individual's Fried frailty index based on data collected by one or more body-worn inertial sensors. The inertial sensor data may be collected during a walking trial, such as a timed-up-and-go (TUG) test. Parameters quantified by the inertial sensor data may be used as input parameters in a model (e.g., a regression model) that assesses the individual's frailty. The model may include all input parameters that have or exceed a threshold level of significance (e.g., $P \geq 0.05$) to the output frailty value. The model may be configured to output frailty values that approximate clinically-measured frailty index values. For example, a linear regression model may be generated to approximate reference, clinically-measured frailty index values of individuals. The output frailty values may be estimated from inertial sensor data generated by the individuals. The linear regression model may be configured to approximate the frailty index value with a high coefficient of determination, or $R^2$ value. A high $R^2$, which can have a maximum value of 1, indicates that the regression model explains a high degree of any patterns and variations in the reference frailty index values. Other measures of a regression model's accuracy, such as sensitivity or specificity, may also be used. They generally measure how often a regression model outputs a frailty classification that matches a reference clinical classification, and are discussed more below.

The regression models may be used to subsequently quantify frailty based on an individual's inertial sensor data. The calculation would no longer require specialized equipment, specialized expertise, or access to a reference sample. Non-experts in a primary care setting may thus be able to use the models to generate a quantitative frailty estimate of their patients. In one example, a linear regression model yielded a $R^2$ value of about 0.39, showing that the frailty quantified by the regression model may also approximate a clinically-measured frailty index value with an accuracy corresponding to $R^2=0.39$.

In some implementations, one or more regression models may output a frailty class rather than a frailty index value. For example, a regression model may output an approximation of whether an individual is frail, pre-frail, or robust based on his or her inertial sensor data. In a more specific example, two logistic regression models may be generated to classify an individual's frailty. Each of the logistic regression models may compare the individual's inertial sensor data against the inertial sensor data collected from individuals who were classified as robust. A first logistic regression model may distinguish between whether the individual is frail or robust. A second logistic regression model may distinguish between whether the individual is pre-frail or robust. The accuracy of the regression models may be measured based on their sensitivity and specificity, which are defined below. In one example, a first logistic regression model yielded an accuracy of about 88%. The first logistic regression model may thus be used to distinguish between frail and robust individuals in a way that closely approximates clinically-based distinctions of frail and robust individuals. In the example, a second logistic regression model yielded an accuracy of 58%. The second logistic regression model may thus be used when more granularity of an individual's frailty class is desired (i.e., whether the individual is pre-frail, a category between frail and robust) and the accuracy in approximating clinically-determined frailty classes is not as important.

The regression models may thus be used to quantify an individual's frailty and to classify the individual's frailty into one of a plurality of frailty classes. The regression models may be implemented by any device, such as software running on a processor, that is configured to receive values of inertial sensor parameters, which are used as inputs in the regression models. The implementation thus provides a quantitative assessment of frailty that may be administered by non-experts in a clinical setting, a primary care setting, a home setting, or any other setting.

BRIEF DESCRIPTION OF THE DRAWINGS

The various advantages of the embodiments of the present invention will become apparent to one skilled in the art by reading the following specification and appended claims, and by referencing the following drawings, in which:

FIG. 1A illustrates a perspective view of an example of an individual performing a walking trial in which inertial sensor data are measured.

FIG. 1B illustrates a perspective view of an example inertial sensor.

DETAILED DESCRIPTION

Figure 2:
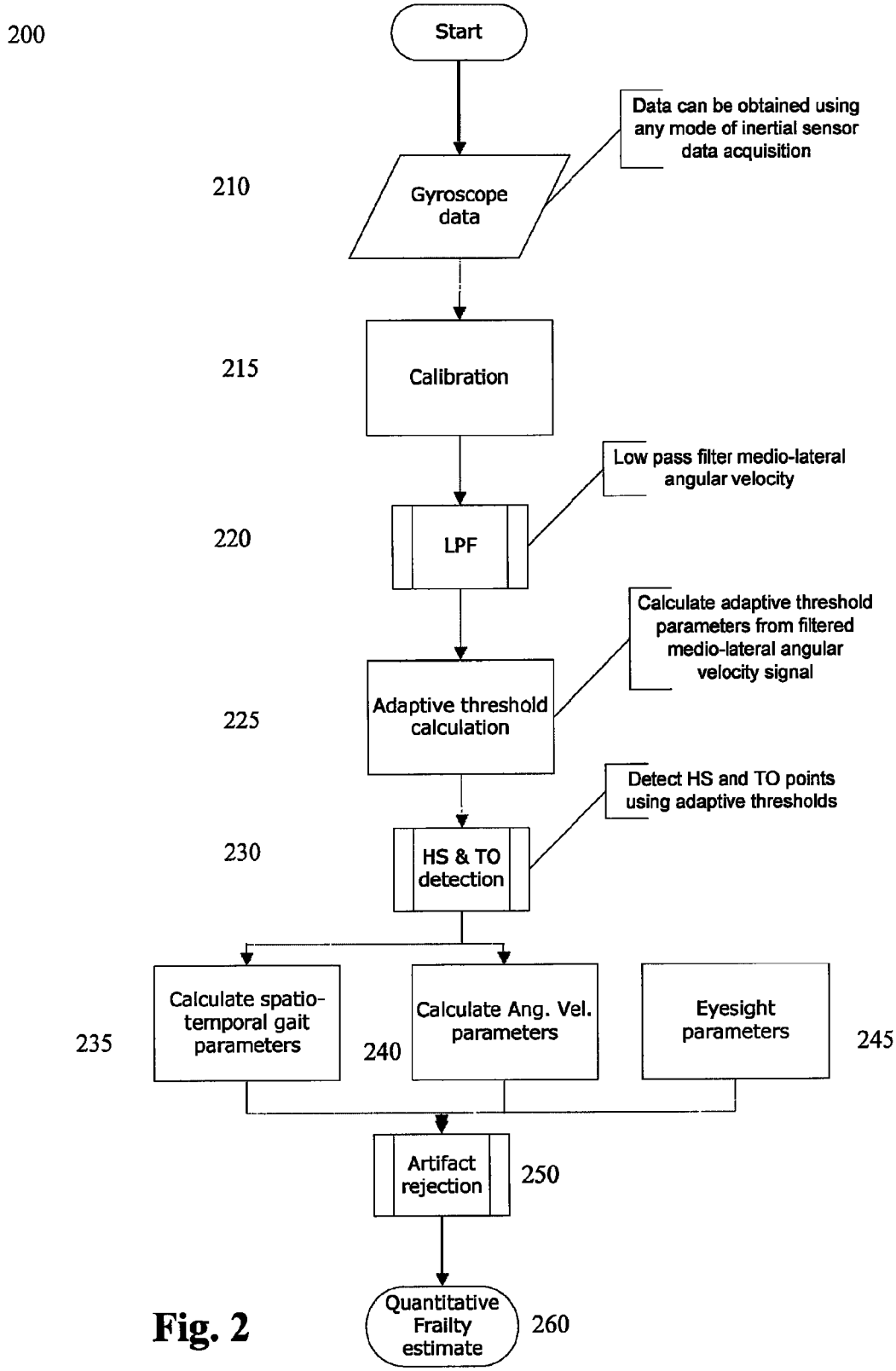
FIG. 2 illustrates example operations of a method in which a quantitative frailty estimate is generated.

Embodiments may provide for a system that generates inertial sensor data from an individual's movement and uses the data to quantify the individual's frailty. The quantified frailty may approximate clinical measures of the individual's frailty, such as the Fried frailty index.

The individual may generate the inertial sensor data during a timed up and go (TUG) test. FIG. 1A illustrates an individual performing the TUG test. During a TUG test, inertial sensors may measure the individual 10's motion as the individual 10 stands up from a chair (e.g., a chair 46 cm high with 65 cm arm rest), walks a distance, such as 3 m, to a designated spot 12, turns around, walks back to the chair, and sits down. Two inertial sensors 14a, 14b may be attached to the individual 10's left and right shanks (e.g., shins) 16a, 16b, respectively, to capture data on the individual 10's motion. In other embodiments, more (e.g., 4) or fewer (e.g., 1) inertial sensors may be used. The sensors may also be attached to other portions of the individual 10's lower body, such as his or her feet or hip. The TUG test may be conducted at a variety of settings, such as in a nursing home, in a community dwelling, or in a clinic or hospital. In one example, inertial sensor data was collected from 235 community dwelling elderly adults as they performed the TUG test.

Sensors 14a, 14b may measure various inertial sensor parameters related to the person's motion. Some parameters include angular velocity parameters, acceleration parameters, spatial gait parameters, and temporal gait parameters. Characteristic points, such as an initial contact with the ground (e.g., a heel strike), a terminal contact with the ground (e.g., a toe-off), and a mid-swing point may be identified from the parameters' values.

Other inertial sensor parameters, such as the time taken to perform the TUG test, may be recorded by a clinician or primary care practitioner administering the test, or may be calculated from the angular velocity data. The time parameters may include the manual TUG time, which begins when the individual 10 is instructed to begin the test and ends when the individual 10 sits back on the chair. The time parameters include a turn time, which identifies the amount of time between the individual 10's first step and the step in which the individual 10 turns from spot 12. The time parameters may further include a return time, which identifies the amount of time between the turn step and the last step taken by the individual 10 in the TUG test.

The sensors may include tri-axial accelerometers, tri-axial gyroscopes, GPS transceivers, passive infrared (PIR) sensors, tilt and vibration sensors, and any other sensor operable to measure movement- or force-related parameters. Each sensor may be configured to measure rotation and acceleration about a X, Y, and Z sensor axis, as illustrated in FIG. 1B. The sensors may be attached to any portion of an individual's lower body, and may be attached by means of tight fitting clothing, elasticized bandages, or any other manner of attachment. The sensor axes may be oriented to align with certain axes of the body. For example, the sensors may be oriented to capture movement about the individual 10's medio-lateral (ML) axis. The sensors may further be oriented such that one sensor axis is oriented to capture movement in the individual's anteroposterior (AP) direction and one sensor axis may be oriented to capture movement in the vertical direction.

FIG. 2 illustrates a method 200 for quantifying frailty from inertial sensor data. The method processes inertial sensor data and uses the data to generate a quantitative frailty estimate based on, e.g., a linear or logistic regression model. At operation 210, inertial sensor data, such angular velocity and acceleration, may be collected by a sensor's gyroscope, accelerometer, PIR sensor, tilt sensor, vibration sensor, or any other sensing component. The data may be obtained using any mode of inertial sensor data acquisition. For example, inertial sensor data may be sampled at a frequency of 102.4 Hz. The sampling rate of the sensors may be configured with firmware (e.g., TinyOS). The sensors may further be configured to wirelessly transmit inertial sensor data using a protocol such as a low-rate wireless personal area network (PAN) or Bluetooth® protocol. In order to ensure that the angular velocity signal derived from the gyroscope has the correct polarity, the "skewness" of the signal (e.g., a measure of the asymmetry of the signal) may be calculated for each walk. If the skewness is less than zero, the gyroscope signal can be inverted to ensure the correct polarity of the signal.

At operation 215, the inertial sensor data may be calibrated. For example, the raw gyroscope and accelerometer data may be calibrated to derive the angular velocity and acceleration vectors with respect to the sensors' unit coordinate axes or some other orientation. In the example, operation 215 may use the sensors' gyroscope data to provide a sensor-to-segment offset orientation matrix (e.g., a rotation matrix) to calibrate the data to derive acceleration and angular velocity vectors with respect to the coordinate axes of each inertial sensor. Any other standard calibration procedure may be used to calibrate the gyroscopes before they are used in the walking trial.

At operation 220, the calibrated inertial sensor data may be filtered before or after transmission from the sensor to remove noise. For example, a zero-phase $5^{th}$ order Butterworth filter may be used to low pass filter the inertial sensor data. The corner frequency (e.g., 50.2 Hz) may be calculated as $$f_c = \left(\frac{f_s}{2} - 1\right),$$

where $f_s$ is the sampling rate. In the example, a low pass filter may be applied to data that measures angular velocity in the medio-lateral direction. A bandpass filter may also be used to filter out low-frequency components of the data.

At operation 225, adaptive thresholds may be calculated based on the angular velocity data. The adaptive thresholds may be used to define the likely range of characteristic points, namely initial contact points, terminal contact points, and mid-swing points. Such points are located generally in local maxima or minima of the angular velocity data. Restricting examination of the angular velocity data to portions isolated by the adaptive thresholds can ensure robust detection of the characteristic points over a variety of walking speeds.

Figure 3A:
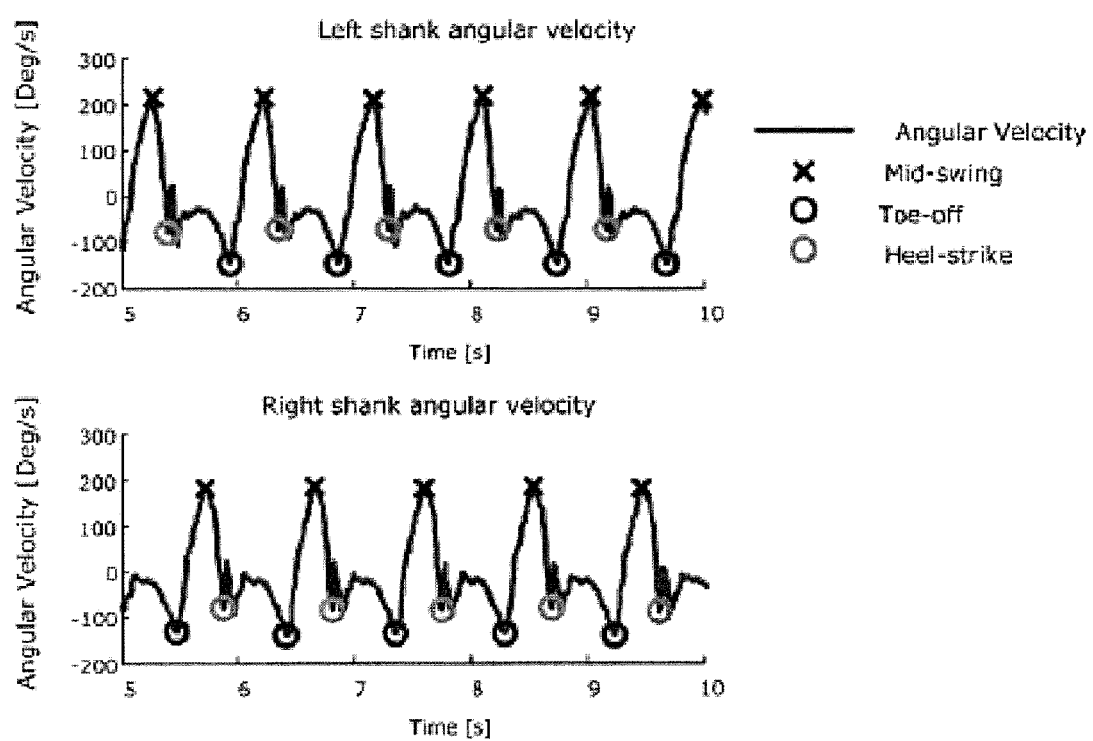
FIG. 3A illustrates example angular velocity data.

For example, angular velocity data and identified characteristic points are shown in FIG. 3A. FIG. 3A shows that the mid-swing point for each gait cycle may be located based on where the angular velocity reaches a local maximum. Robust detection of the mid-swing point may be ensured by requiring that a particular local maximum be greater than a preceding local maximum by more than an adaptive threshold $th_1$ rad/sec. In one example, adaptive threshold $th_1$ may be calculated as $$th_1 = 0.6 \cdot \max(\omega_{ML}), \quad (1)$$

where $\omega_{ML}$ is the medio lateral angular velocity. The local maximum, mid-swing point may further be verified to have an angular velocity above a second adaptive threshold $th_2$, where $$th_2 = 0.8 \cdot \frac{1}{N} \sum_{i=1}^{N} (\omega_{ML_i} > \varpi_{ML}) \quad (2)$$

Moreover, if two maximum peaks are found within $t_1$ seconds of each other, only the greater maximum can be considered, wherein $t_1$ may be defined as 0.5 seconds or $f_s*1.5$ and $f_s$ is defined as the stride frequency.

The adaptive thresholds may further be used to identify, at operation 230, initial contact points (e.g., heel strike points) and terminal contact points (e.g., toe-off points). FIG. 3A shows identification of initial contact (e.g., heel strike) points and terminal contact (e.g., toe-off) points. An initial contact point may be located at where angular velocity reaches a local minimum. For the local minimum to be identified as an initial contact point, it may be required to have a preceding maximum that is greater than the minimum by an adaptive threshold $th_3$ rad/sec, where $$th_3 = 0.8 \cdot \left| \frac{1}{N} \sum_{i=1}^{N} (\omega_{ML_i} < \varpi_{ML}) \right| \qquad (3)$$

The local minimum for the initial contact point may further be required to be less than adaptive threshold $th_5$ rad/sec, where $$th_5 = \text{mean}(\omega_{ML}) \qquad (4)$$

A terminal contact point may be located at a local minimum that has an angular velocity less than adaptive threshold $th_4$ and that has a preceding maximum that is greater than adaptive threshold $th_6$, where $$th_4 = 0.8 \cdot \frac{1}{N} \sum_{i=1}^{N} (\omega_{ML_i} < \varpi_{ML}) \qquad (5)$$

$$th_6 = 2 th_3 \qquad (6)$$

In identifying initial contact and terminal contact points, only data within $t_2$ seconds may be considered. In one example $t_2$ may be defined as 1.5 seconds for $f_s*1.5$. Specific values and ranges are provided as examples only, and other values and ranges may be used as appropriate.

At operation 235, spatio-temporal parameters of the individual 10's measured gait may be calculated. The parameters may include measurements such as the individual 10's cadence, number of gait cycles, number of steps taken, stance time, step time, swing time, single support percentage, double support percentage, and stride time, that may be included in a regression model. The parameters may further include statistical derivations of the measurements, such as such as their mean, maximum, range, and coefficient of variation (CV).

The number of gait cycles may be calculated as the number of initial contact (e.g., heel strike) points minus one, and may represent the number of complete gait cycles. The cadence may measure the number of steps per minute, and may be calculated as the number of steps divided by the TUG walking time (in units of minutes). The step time may be calculated as the time between the initial-contact (e.g., heel-strike) point on one foot and the initial contact point on the other foot. The stride time may be calculated as the time from initial contact (e.g., heel-strike) of one foot to a subsequent initial contact of the same foot. Stance time may be calculated as the time from an initial contact (e.g., heel-strike) point to a terminal contact (e.g., toe-off) point on the same foot. Swing time may be calculated as the time from a terminal contact (e.g., toe-off) point to a initial contact (e.g., heel-strike) point on the same foot. Double support percentage may be determined by calculating the percentage of each gait cycle during which both feet are in contact with the ground (where the gait cycle can be calculated as the time between successive initial contact points (e.g., heel-strike points)). Single support percentage for a foot may be defined as the swing duration of the other foot expressed as a percentage of gait cycle time.

Figure 3B:
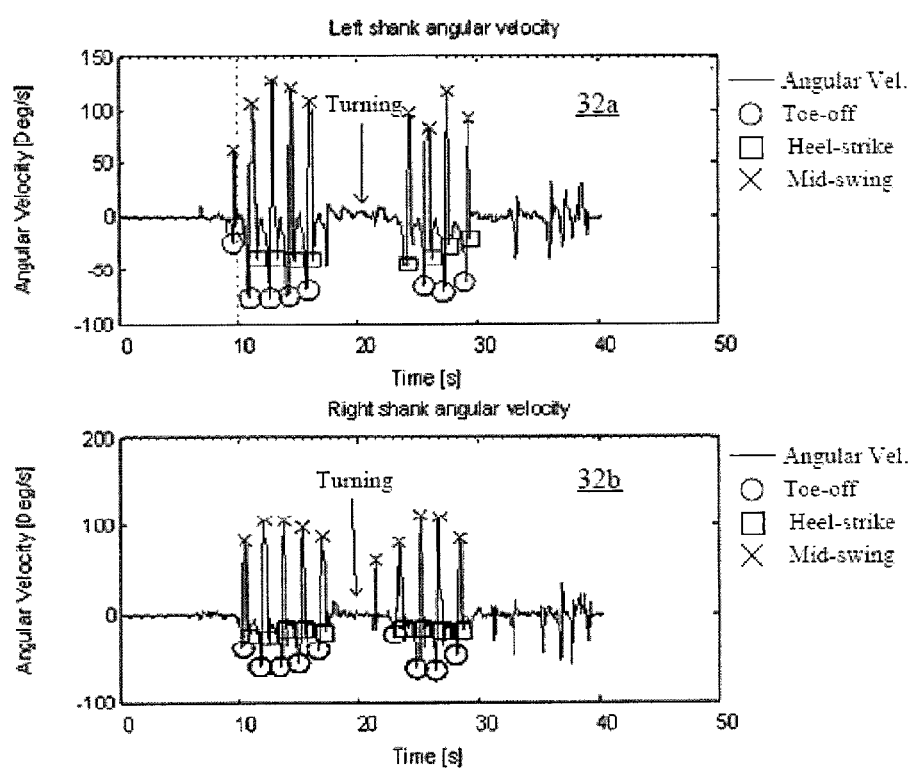
FIG. 3B illustrates example angular velocity data.

The angular velocity data may be used to determine inertial sensor parameters like TUG time segments, which include a walk time, turn time, and return time. FIG. 3B illustrates example angular velocity data that may be used to identify when an individual is stopped, is walking, and is turning. For example, the data in FIG. 3B may show that the individual is stopped for the first ten seconds, is rising from a seat and walking to a designated spot for about the next ten seconds, is turning after a total of about twenty seconds, and is returning to the seat and sitting after a total of about thirty seconds.

Operation 240 demonstrates that in addition to the spatio-temporal gait parameters, the derived parameters may include one or more parameters that are obtained directly from the angular velocity data. The angular velocity data may be divided among along the sensor's Y, X, and Z axes. The axes may correspond to an individual's medio-lateral (ML), antero-posterior (AP), and V directions. These angular velocity parameters could include parameters to detect and analyze the speed and timing of an individual's turn during the TUG test. For example, the mean, minimum and maximum angular velocities (averaged across both shanks) during the walk, expressed in degrees per second, may each be determined in the Y, X, and Z axes (which may correspond to, for example, the ML, AP and V directions). The measurements may form a set of nine (i.e., 3×3) tri-axial angular velocity parameters. Further, the coefficient of variation (CV) of the parameters may also be calculated. The CV of a parameter may be defined as the ratio of the parameter's standard deviation to its mean.

The tri-axial set of angular velocities may also be multiplied by the height of the individual performing the TUG test in order to obtain a variable approximately proportional to the linear velocity of the shank. This approximation can be based on the formula for linear velocity, which equals the radius times angular velocity, wherein the radius is the leg length and height is assumed to be approximately proportional to the leg length. Thus, the linear velocity may be specifically related to the shank/foot of the individual as opposed to merely the trunk of the individual. In addition, other angular velocity-based parameters such as turn angular velocity may be calculated. The turn angular velocity can be defined as the mean amplitude (taken across both shanks) of the angular velocity signal at the turn point for each shank.

At operation 245, the individual 10's eyesight may also be measured, such as on a Binocular logmar or a Pelli-Robson contrast sensitivity scale.

At operation 250, artefact rejection may be performed. The artefact rejection may be configured to remove spurious temporal parameters that might have been calculated from erroneous gyroscope data. The artefact rejection routine may be designed to account for missing and extra initial contact and terminal contact points. Further, the artefact rejection may be based on two strands: examining temporal sequence information, and examining times between successive characteristic points (e.g., gait cycle information).

Temporal sequence information may be obtained based on the following: once all characteristic points (e.g., initial contact points, terminal contact points) are detected, each point may be assigned a numerical label of one to four. For example, an initial contact point on the right foot is assigned 1; a terminal contact point on the left foot is assigned 2; an initial contact point on the left foot is assigned 3; and a terminal contact point on the right foot is assigned 4. A correct gait cycle (if starting on a right initial contact point) would then follow the sequence 1, 2, 3, 4. By subtracting each label from the previous label, spurious samples (e.g., samples not producing a difference equal to either −3 or 1) may be deemed artefacts and rejected.

The time between successive characteristic points (e.g., gait cycle information) may be calculated for each set of four left and right initial contact and terminal contact points. This calculation may be referred to as "gait cycle time." If the difference between any successive characteristic point is greater than a particular time threshold (e.g., 2.5 seconds), the associated characteristic point could be identified as an artefact. Similarly, if the difference between any successive characteristic point is zero seconds, the associated point may be flagged as an artefact. Furthermore, any gait parameters with a negative or zero value may also be rejected.

The collection and processing of inertial sensor and other data in operations 210 to 250 are described in more detail in co-pending applications entitled "WIRELESS SENSOR BASED QUANTITATIVE FALLS RISK ASSESSMENT," U.S. application Ser. No. 12/782,110; and "A METHOD FOR BODY-WORN SENSOR BASED PROSPECTIVE EVALUATION OF FALLS RISK IN COMMUNITY-DWELLING ADULTS," U.S. application Ser. No. 13/186,709, both of which are incorporated herein by reference.

At operation 260, the processed values of the inertial sensor parameters may be used to generate a quantitative frailty estimate. The quantitative frailty estimate may approximate a clinically-measured frailty metric. The metric may be a Fried frailty index value, a frailty class based on the index value, or any other frailty metric. In one example, a linear regression model may quantify an individual's frailty. The quantity outputted by the linear regression model may further be an estimate of what a clinically-measured frailty index value for the individual would have been. In one example, a logistic regression model may classify the individual's frailty level as pre-frail, frail, or robust. The class outputted by the logistic regression model may correspond to the classes defined by Fried, and may estimate what a clinically-measured classification for the individual would have been. The regression models may output their estimates based on inertial sensor data generated by the individual.

The regression models may initially be generated from reference Fried frailty index values and classifications that were obtained, for example, in a clinical setting using the Fried standard method. The Fried standard method may determine an index value based on three or more of the following five criteria: unintentional weight loss, self-reported exhaustion, weakness (e.g., lowered grip strength), slow walking speed, and low physical activity. The frailty index value may quantify the combination of the frailty criteria as number from 0 to 5. An index value of 0 classifies the individual as robust. An index value of 1-2 classifies the individual as pre-frail. An index value of 3-5 classifies the individual as frail.

The frailty index values may be used to generate a regression model that approximates the index values using inertial sensor data. The regression model may be used to subsequently estimate an individual's frailty index value or frailty class from the individual's inertial sensor data. By using the generated regression model, the individual's frailty may later be quantified without a separate analysis of Fried's five frailty criteria and without the need for personnel having statistical expertise. Rather, the individual's frailty may be quantified with one or more inertial sensors attached to the individual and a processor that implements the regression model. The quantified frailty may be treated as an estimate of a clinically-measured frailty metric.

In some implementations, a linear regression model may be generated at operation 260 to estimate a frailty index value. The input to the linear regression model may comprise any inertial sensor parameter quantified by the inertial sensor data. If the data generates a large quantity of parameters, the number of parameters included in the model may be reduced. For example, all the inertial sensor parameters may be grouped into blocks in terms of general characteristics. To generate the linear regression model, a series of linear regression analyses may be performed on the parameters and on all two-way interactions of parameters in each block. The linear regression analyses may determine the significance (e.g., p-value) of any relationship between the reference frailty index values and each inertial sensor parameter or two-way interaction. In the linear regression analyses, the reference frailty index value may be treated as the dependent variable while the inertial sensor parameter or two-way interaction may be treated as an independent variable. Independent variables that have insufficient significance to the dependent variable, such as those having $p<0.05$, may be excluded from the linear regression model being generated. The remaining variables, or parameters, from each block may be combined into a final linear regression model. An example of inertial sensor parameters and two-way interactions that are included in a linear regression model is shown in Table 1. The inertial sensor parameters and two-way interactions form the input that is used to estimate a frailty index value.

TABLE 1

| | |
|---|---|
| Mean single support (%) | Mean AP Ang. vel. |
| Cadence | Min AP Ang. vel. |
| Mean ML ang. Vel | No steps |
| Max ML ang vel. | Mean single support:Cadence |
| Min ML ang. vel. | Max ML ang. vel.:Min ML ang. vel. |
| Time of turn | Time of turn:Turn ang. vel. |
| ML ang. vel. at turn | Mean AP ang. Vel.:Min AP ang. vel. |
| Max AP ang. vel. | Max AP ang. vel.:No steps |

The association of each quantitative parameter with the Fried frailty index may further be examined using Pearson's correlation coefficient. Separate coefficients may be calculated for male individuals and female individuals. Table 2 shows example results of bivariate correlations that yielded the absolute value of Pearson's correlation coefficient between each of a group of inertial sensor parameters and reference frailty index values. Parameters in the table are ranked according to the absolute value of the coefficient.

TABLE 2

| Variable | Absolute value of Pearson's Correlation Coefficient |
|---|---|
| Walk time | 0.55 |
| Time of turn | 0.55 |
| Return time | 0.55 |
| Number of steps | 0.49 |
| Mean time to turn | 0.46 |
| Gait cycles | 0.45 |
| TUG recording time | 0.40 |
| Mean mid-swing points | 0.39 |
| Max mediolateral angular velocity × height | 0.37 |
| Min AP angular velocity | 0.36 |

TABLE 2-continued

| Variable | Absolute value of Pearson's Correlation Coefficient |
|---|---|
| Mean stride velocity | 0.36 |
| Max mediolateral angular velocity | 0.34 |
| Min mediolateral angular velocity × height | 0.34 |
| Mean stride length | 0.33 |
| Min mediolateral angular velocity | 0.31 |
| Cadence | 0.29 |
| Min vertical angular velocity × height | 0.29 |
| Min AP angular velocity × height | 0.29 |
| Max AP angular velocity × height | 0.27 |
| Max vertical angular velocity | 0.27 |
| Max AP angular velocity | 0.26 |
| Mean AP angular velocity | 0.26 |
| Coefficient of variation of stride length | 0.25 |
| Mean stance time | 0.24 |
| Max vertical × height | 0.23 |
| Mean mediolateral angular velocity × height | 0.23 |
| Min vertical angular velocity | 0.22 |
| Mean vertical angular velocity | 0.22 |
| Mean single support | 0.21 |
| CV stride velocity | 0.21 |
| Mean ML angular velocity | 0.21 |
| Range of mid-swing points | 0.20 |
| Mean turn ratio | 0.20 |
| Mean stride time | 0.15 |

Figure 4:
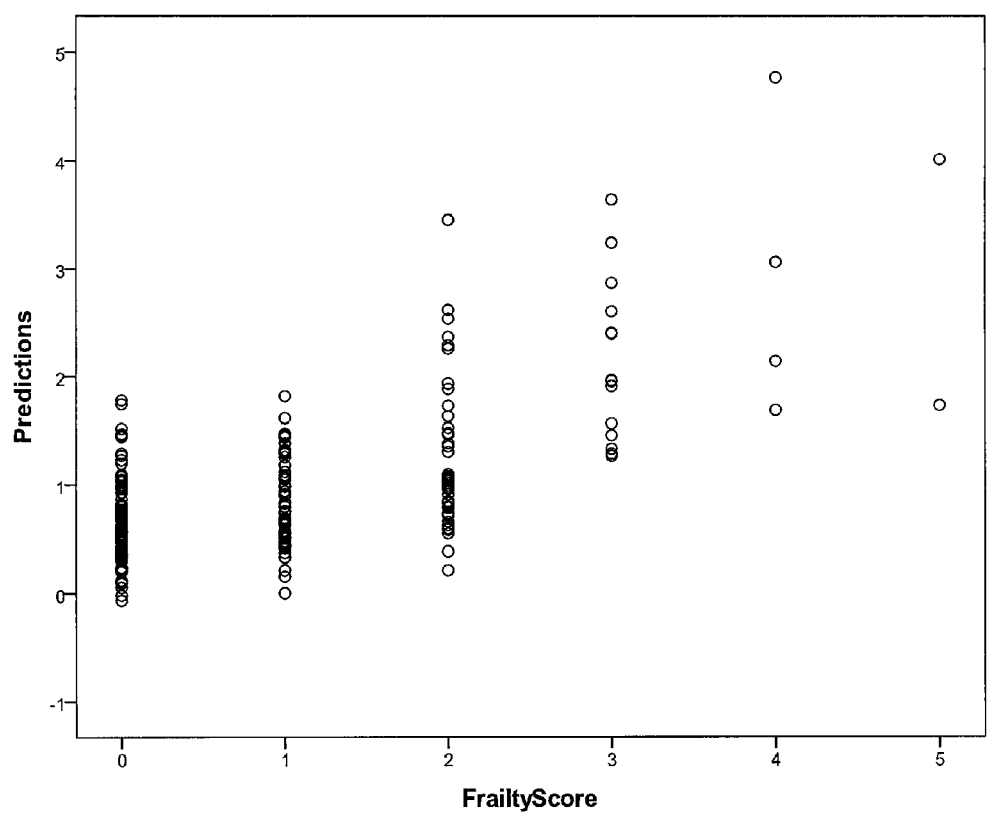
FIG. 4 illustrates example estimates and clinical measurements of individuals' Fried frailty index scores.

The performance of the linear regression model may be measured with a $R^2$ value, which determines how well the model explains the variation in the output. For example, the $R^2$ may measure whether variations in reference frailty index values can be explained by a linear combination values of inertial sensor parameters. A $R^2$ value equal to zero implies that none of the variation is explained while a unity value means that all the variation in the output, reference index values is explained by the linear regression model. One example linear regression model yielded a $R^2$ value of 0.3873, suggesting that approximately 39% of variation in reference frailty index values is explained by the model. FIG. 4 shows a plot comparing clinically-measured frailty index values determined by the Fried standard method and the frailty index values estimated by the linear regression model. The plot shows a positive relationship and that the Fried frailty index value can be approximated by the linear regression model.

In addition to or instead of estimating an individual's frailty index value, the individual's frailty class (e.g., pre-frail, frail, or robust) may be estimated. In one example, the frailty class may be approximated through two separate models. A first model may be based on dichotomous comparisons of individuals clinically classified as frail against individuals clinically classified as robust, in which the latter may serve as a reference class. A second model may be based on dichotomous comparisons of individuals clinically classified as pre-frail against the individuals in the reference class. The comparisons may be based on the inertial sensor data generated by the individuals in one class versus inertial sensor data generated by individuals in the reference class. The first model may estimate whether the individual is in the pre-frail class or is in the robust class. The second model may estimate whether the individual is in the frail class or is in the robust class. In one example, the regression model may be a logistic regression model.

The input to the logistic or any other regression model may comprise any inertial sensor parameter quantified by the inertial sensor data. Like with the linear regression model, the number of input parameters may be reduced by grouping the parameters into blocks and performing a logistic regression analysis on all parameters and on all two-way interactions between parameters in each block. The regression analyses may identify parameters that do not have a significant relationship (e.g., $p<0.05$) with the logistic model's dependent parameter, which may comprise frailty classes that were clinically measured. The inertial sensor parameters that are not significant may be excluded from the final logistic regression model, while the significant parameters may be included. In order to obtain unbiased generalized models, each model was validated using 1000 random sub-sampling cross validation. Table 3 shows inertial sensor parameters that are included in an example logistic regression model that distinguishes between pre-frail versus robust individuals and in an example logistic regression model that distinguishes between frail versus robust individuals.

TABLE 3

| Model 1 Pre-Frail Vs Robust | Model 2 Frail Vs Robust |
|---|---|
| Mean double Support | Mean single support |
| Mean single Support | Cadence |
| CV double Support | Max ML ang. vel. |
| CV stride Time | Mean single support:Cadence |
| Min AP ang. vel. | |
| Mean AP Angle Velocity | |
| Mean double support:Mean single support | |
| CV double support:CV stride time | |
| Min AP ang. vel.:Mean AP ang. vel. | |

Multinomial regression analysis may be used to compare how well the first and second models distinguish against individuals in a robust group. For example, one multinomial regression analysis was performed with a group of 110 individuals clinically classified as pre-frail, 102 individuals clinically classified as robust, and 23 individuals clinically classified as frail. The analysis in the example showed that pre-frail patients may tend to be less different when compared with robust individuals than when compared with frail individuals. Table 4 below shows that the class of frail individuals in one example had more parameters that were significantly different (as shown by low P-values) from the robust class.

TABLE 4

| Pre-Frail (N = 110) | Frail (N = 23) |
|---|---|
| Walk time (p = 0.001) | Mean single support (p < .001) |
| Gait cycles (p = 0.009) | Mean stance time (p < .001) |
| No steps (p = 0.01) | Mean stride time (p = 0.003) |
| Return time (p < 0.001) | CV stride time (p = 0.03) |
| Time of turn (p = 0.007) | CV step time (p = 0.013) |
| Min AP ang. vel. (p = 0.013) | Mean ML Ang. Vel. (p < .001) |
| Mean stride velocity (p = 0.001) | Max ML Ang. Vel. (p < .001) |
| Means stride length (p = 0.002) | Min ML Ang. Vel. (p < .001) |
| CV stride length (p = 0.01) | Walk time (p < 0.001) |
| Mean turning time (p = 0.026) | Gait cycles (p < 0.001) |
| | No steps (p < 0.001) |
| | Cadence (p < 0.001) |
| | Walk ratio (p = 0.013 |
| | Return time (p < 0.001) |
| | Range of mid swing points (p = 0.002) |
| | Mean mid-swing points (p <0.001) |
| | Time of turn (p < 0.001) |
| | TUG recording time (p < 0.001) |
| | Mean AP Ang. Vel. (p < 0.001) |
| | Max AP Ang. Vel. (p < 0.001) |
| | Min AP Ang. Vel. (p < 0.001) |
| | Mean V. Ang. Vel. (p = 0.002) |
| | Max V. Ang. Vel. (p < 0.001) |

TABLE 4-continued

| Pre-Frail (N = 110) | Frail (N = 23) |
|---|---|
| | Min V. Ang. Vel. (p = 0.001) |
| | Mean stride velocity (p < 0.001) |
| | CV stride velocity (p = 0.005) |
| | Mean stride length (p < 0.001) |
| | CV stride length (p < 0.001) |
| | Mean turning time (p < 0.001) |
| | Mean turn ratio (p < 0.001) |
| | Mean ML ang. Vel. × Height (p < 0.001) |
| | Max ML ang. Vel. × Height (p < 0.001) |
| | Min ML ang. Vel. × Height (p < 0.001) |
| | Max AP ang. Vel. × Height (p < 0.001) |

The performance of the logistic regression model in classifying individuals into a frailty class may be quantified using sensitivity ("sens") and specificity ("spec"). Sensitivity may be calculated as the proportion of pre-frail or frail individuals (e.g., individuals having a Fried frailty index value of 1-2 and 3-5, respectively) "correctly" identified by the logistic regression model. An identification by the logistic regression model may be considered correct if it matches a reference, clinically-measured classification. Specificity may be calculated as the proportion of robust individuals (e.g., individuals having a frailty index value of 0) "correctly" identified by the logistic regression model. Table 5 shows example sensitivity and specificity values for the two logistic regression models discussed above. The table shows that the model distinguishing between pre-frail and robust individuals has an average accuracy of 57.9%, while the model distinguishing between frail and robust individuals has an average accuracy of 87.2%.

TABLE 5

|  | Model 1 | Model 2 |
|---|---|---|
| Sens (%) | 61.3 | 87.8 |
| Spec (%) | 54.4 | 86.8 |

The logistic regression model that distinguishes between robust and frail individuals, such as Model 2, may thus be used to distinguish between frail and robust individuals in a way that closely approximates clinically-based distinctions of frail and robust individuals. The logistic regression model that distinguishes between robust and pre-frail individuals, such as Model 1, may not have as high a degree of accuracy, but provides a more granular determination of an individual's frailty level.

Generation of regression models is discussed in more detail in co-pending application "WIRELESS SENSOR BASED QUANTITATIVE FALLS RISK ASSESSMENT," U.S. application Ser. No. 12/782,110, which is incorporated herein by reference.

The operations described above may be implemented in executable software as a set of logic instructions stored in a machine- or computer-readable medium of a memory such as random access memory (RAM), read only memory (ROM), programmable ROM (PROM), firmware, flash memory, etc., in fixed-functionality hardware using circuit technology such as application specific integrated circuit (ASIC), complementary metal oxide semiconductor (CMOS) or transistor-transistor logic (TTL) technology, or any combination thereof. For example, computer program code to carry out operations may be written in any combination of one or more programming languages, including an object oriented programming language such as Java, Smalltalk, C++ or the like and conventional procedural programming languages, such as the "C" programming language or similar programming languages.

Embodiments of the present invention are applicable for use with all types of semiconductor integrated circuit ("IC") chips. Examples of these IC chips include but are not limited to processors, controllers, chipset components, programmable logic arrays (PLA), memory chips, network chips, and the like. In addition, in some of the drawings, signal conductor lines are represented with lines. Some may be thicker, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments of the present invention are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments of the invention. Further, arrangements may be shown in block diagram form in order to avoid obscuring embodiments of the invention, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments of the invention, it should be apparent to one skilled in the art that embodiments of the invention can be practiced without, or with variation of, these specific details. The description is thus to be regarded as illustrative instead of limiting.

Those skilled in the art will appreciate from the foregoing description that the broad techniques of the embodiments of the present invention can be implemented in a variety of forms. Therefore, while the embodiments of this invention have been described in connection with particular examples thereof, the true scope of the embodiments of the invention should not be so limited since other modifications will become apparent to the skilled practitioner upon a study of the drawings, specification, and following claims.

We claim:

1. A computer-implemented method for estimating frailty, the method comprising:
   receiving a first reference frailty index value associated with a first individual, a second reference frailty index value associated with a second individual;
   receiving a first set of inertial sensor data associated with the first individual and a second set of inertial sensor data associated with the second individual, wherein the first set of inertial sensor data and second set of inertial sensor data comprise angular velocity data and acceleration data;

generating a linear regression model that outputs a first frailty value estimate based on the first set of inertial sensor data and that outputs a second frailty value estimate based on the second set of inertial sensor data; and storing the linear regression model in a non-transitory computer-readable medium, wherein the linear regression model is based on the difference between the first frailty value estimate and the first reference index value and based on the difference between the second frailty value estimate and the second reference index value.

2. The method of claim 1, further comprising:

receiving a third reference index value associated with a third individual; and receiving a third set of inertial sensor data, wherein the linear regression model is configured to output a third frailty value estimate based on the third set of inertial sensor data, and wherein the linear regression model is further based on the difference between the third frailty value estimate and the third reference index value.

3. The method of claim 2, further comprising:

associating the first reference frailty index value with a reference robust class and associating the second reference frailty index value with a reference frail class, wherein the first reference frailty index value is different than the second reference frailty index value; and generating a first logistic regression model that outputs a first frailty class estimate based on the first set of inertial sensor data and that outputs a second frailty class estimate based on the second set of inertial sensor data, wherein the first logistic regression model is based on one or more differences between the first set of inertial sensor data and the second set of inertial sensor data.

4. The method of claim 3, further comprising:

associating the third reference index value with a pre-frail class, wherein the third reference index value is different than the first reference index value and the second reference index value; and generating a second logistic regression model that outputs a third frailty class estimate based on the third set of inertial sensor data, wherein the second logistic regression model is based on one or more differences between the first set of inertial sensor data and the third set of inertial sensor data.

5. An apparatus comprising one or more processors, the one or more processors configured to receive a first reference frailty index value associated with a first individual, a second reference frailty index value associated with a second individual;

receive a first set of inertial sensor data associated with the first individual and a second set of inertial sensor data associated with the second individual, wherein the first set of inertial sensor data and second set of inertial sensor data comprise angular velocity data and acceleration data;

generate a linear regression model that outputs a first frailty value estimate based on the first set of inertial sensor data and that outputs a second frailty value estimate based on the second set of inertial sensor data; and store the linear regression model in a non-transitory computer-readable medium, wherein the linear regression model is based on the difference between the first frailty value estimate and the first reference index value and based on the difference between the second frailty value estimate and the second reference index value.

6. The apparatus of claim 5, wherein the one or more processors are configured to:

receive a third reference index value associated with a third individual; and receive a third set of inertial sensor data, wherein the linear regression model is configured to output a third frailty value estimate based on the third set of inertial sensor data, and wherein the linear regression model is further based on the difference between the third frailty value estimate and the third reference index value.

7. The apparatus of claim 6, wherein the processors are further configured to:

associate the first reference frailty index value with a reference robust class and associate the second reference frailty index value with a reference frail class, wherein the first reference frailty index value is different than the second reference frailty index value; and generate a first logistic regression model that outputs a first frailty class estimate based on the first set of inertial sensor data and that outputs a second frailty class estimate based on the second set of inertial sensor data, wherein the first logistic regression model is based on one or more differences between the first set of inertial sensor data and the second set of inertial sensor data.

8. The apparatus of claim 7, wherein the one or more processors are further configured to:

associate the third reference index value with a pre-frail class, wherein the third reference index value is different than the first reference index value and the second reference index value; and generate a second logistic regression model that outputs a third frailty class estimate based on the third set of inertial sensor data, wherein the second logistic regression model is based on one or more differences between the first set of inertial sensor data and the third set of inertial sensor data.

* * * * *